US005295402A

United States Patent [19]

[11] Patent Number: 5,295,402

[45] Date of Patent: Mar. 22, 1994

Bovenkerk

[54] METHOD FOR ACHIEVING HIGH PRESSURE USING ISOTOPICALLY-PURE DIAMOND ANVILS

[75] Inventor: Harold P. Bovenkerk, Worthington, Ohio

[73] Assignee: General Electric Company, Worthington, Ohio

[21] Appl. No.: 775,863

[22] Filed: Oct. 15, 1991

[51] Int. Cl.$^5$ ..................... G01N 1/28

[52] U.S. Cl. ..................... 73/864.91; 425/77

[58] Field of Search ....... 73/864.91; 425/77, DIG. 26

[56] References Cited

U.S. PATENT DOCUMENTS

| | | | |
|---|---|---|---|
| 3,079,505 | 2/1963 | Weir et al. | 356/244 X |
| 3,509,597 | 5/1970 | Kirk | 356/244 X |
| 3,895,313 | 7/1975 | Seitz | 331/94.5 D |
| 4,602,377 | 7/1986 | Schiferl et al. | 378/80 X |
| 4,776,223 | 10/1988 | Moss | 73/864.91 |
| 4,970,396 | 11/1990 | Wong | 356/244 X |

FOREIGN PATENT DOCUMENTS

| | | |
|---|---|---|
| 0206820 | 12/1986 | European Pat. Off. . |
| 2239011A | 6/1991 | United Kingdom . |

OTHER PUBLICATIONS

Applied Physics Letters, vol. 47, No. 9, pp. 941–943, Nov. 1985, J. Koskinen et al. "Wear & Hardness of diamondlike coating prepared by ionbeam deposition".

J. Mater. Res, vol. 2, No. 5, pp. 614–617, Sep./Oct. 1987 Arthur L. Ruoff et al. "Synthetic Diamonds produce pressure3 of 125 GPa (1.25 mbar)".

Meyers encyclopedia or physical science and technology, vol. 6, pp. 492–506 published 1987 "High–Pressure Synthesis (Chemistry)" R. H. Wentorf Jr. et al.

Science, vol. 241, Aug. 1988 pp. 913–921 "Low-Pressure Metastable Growth of Diamond and Diamondlike" Phases; John L. Angus et al.

Abstract of Japanese patent 59-164610 published Jan. 24, 1985 vol. 9, No. 17 (C-262) (1740).

*Primary Examiner*—Tom Noland

[57] ABSTRACT

Broadly, the present invention is directed to a method for achieving high pressure wherein a sample is placed between a pair of diamond anvils and the anvils compressed. The improvement comprises forming the anvils from one or more of isotopically-pure $^{12}C$ or $^{13}C$ diamond. Isotopically-pure $^{13}C$ diamond is preferred as it has the highest atomic or bond density parameter of any known material and, therefore, should have the highest hardness also Isotopically-enriched diamond $^{13}C$ diamond should find utility as an anvil with higher $^{13}C$ contents increasing the hardness of the anvil product. By utilizing isotopically pure diamond anvils, less breakage at current pressures should be realized concomitant with the ability to achieve yet higher pressures.

4 Claims, 1 Drawing Sheet

18

10

14

12

16

METHOD FOR ACHIEVING HIGH PRESSURE USING ISOTOPICALLY-PURE DIAMOND ANVILS

BACKGROUND OF THE INVENTION

The present invention is directed to the generation of static pressure by squeezing samples between a pair of anvils and more particularly to achieving higher static pressure utilizing isotopically-pure diamond anvils.

The generation of high pressure for research and development exploratory work has been influenced heavily by apparatus design and strength of materials. Professor Bridgman of Harvard found that he could reach pressures of about 100 Kbar by squeezing thinned samples between flat blocks. This work, starting about 50 years ago, led to the development of the famous Bridgman anvil. Bridgman recognized that if harder materials, such as sintered diamonds, were used for anvils, even higher pressures could be reached. Von Valkenburg and Weir at the National Bureau of Standards (NBS), Washington, D.C., unaware of Bridgman's recommendation, made Bridgman anvils out of single crystal diamond in 1959. This started a revolution in high pressure work. Diamond anvil cells now are ubiquitous devices used throughout the world in high pressure research.

Twenty years later, NBS high pressure cells achieved pressures up to 500 Kbar utilizing anvils, each of which was a brilliant cut diamond of about one-third carat, the culet being polished to produce a flat of about 0.002 $mm^2$ in area. This flat generally is the (100) plane, since the normal plane of a brilliant cut is (100).

Pressures approaching 5,000 Kbar, equal to the pressure at the center of the earth, have been reported by Ruoff et al, "Optical Properties of Diamond at Pressures Comparable to the Earth's Center", *Proceedings of the Second International Conference, New Diamond Science and Technology*, Edited by Messier et al, Sep. 23–27, Washington, D.C. Materials Research Society, Pittsburgh, Pa., the disclosure of which is expressly incorporated herein by reference. Still higher pressures are desired. Experiments performed at 4,000 Kbar and higher results in the expensive anvils being broken in virtually every run. Thus, the need in the art for apparatus that is capable of producing these or even higher pressures without loss or breakage of the diamond anvils.

BROAD STATEMENT OF THE INVENTION

Broadly, the present invention is directed to a method for achieving high pressure wherein a sample is placed between a pair of diamond anvils and the anvils compressed. The improvement comprises forming the anvils from one or more of isotopically-pure $^{12}C$ or $^{13}C$ diamond. Isotopically-pure $^{13}C$ diamond is preferred as it has the highest atomic or bond density parameter of any known material and, therefore, should have the highest hardness also. Isotopically-enriched diamond $^{13}C$ diamond should find utility as an anvil with higher $^{13}C$ contents increasing the hardness of the anvil product. By utilizing isotopically pure diamond anvils, less breakage at current pressures should be realized concomitant with the ability to achieve yet higher pressures. For present purposes, isotopically-pure diamond contains greater than 99.1 wt-% isotope content.

BRIEF DESCRIPTION OF THE DRAWING

The drawing is an enlarged cross-section of an opposed diamond-anvil cell, showing a metal gasket confining the sample. The drawing will be described in detail below.

DETAILED DESCRIPTION OF THE INVENTION

Figure 1:
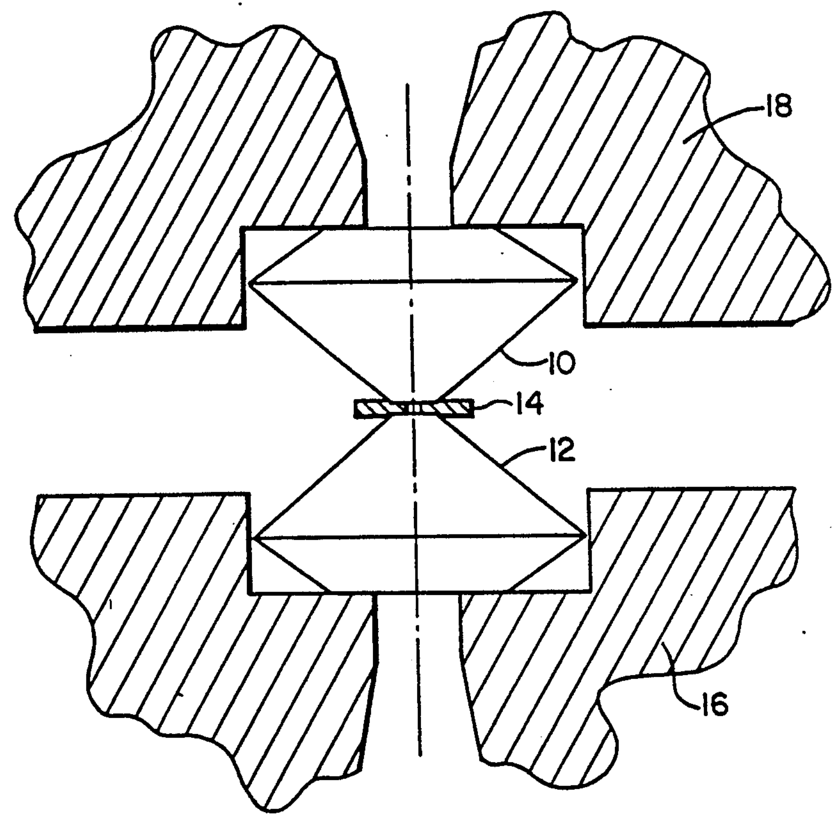

The construction and operation of diamond anvil high pressure cells now is well known and such constructions are appropriate utilizing the isotopically pure diamond anvils of the present invention. In this regard, reference is made to the following publications which are expressly incorporated herein by reference: Field, *The Properties of Diamond*, Academic Press, New York City, N.Y. (1979); Manghnani, et al., *High-Pressure Research and Mineral Physics*, Terra Scientific Publishing Company, Tokyo, American Geophysical Union, Washington, D.C. (1987); Homan, "Higher Pressure in Science and Technology", *Mat. Res. Soc. Symp. Proc.*, vol. 22, pp 2939, et seq., Elsevier Science Publishing Company (1984); Vodar, et al., *High Pressure Science and Technology, Proceedings of the VIIth International AIRTAPT Conference*, Le Creusot, France, Jul. 30–Aug. 3, 1979, Pergamon Press, New York, N.Y.; Ruoff et al, "The Closing Diamond Anvil Optical Window in Multimegabar Research", *J. Appl. Phys.*, 69 (9), 6413–6415, May 1, 1991; Mao et al, "Optical Transitions in Diamond at Ultrahigh Pressures", *Nature*, Vol. 351, 721 et seq, Jun. 27, 1991; and Ruoff et al, "Synthetic Diamonds Produce Pressure of 125 GPa (1.25 Mbar)", *J. Mater. Res.*, 2 (5), 614–617, September/October 1987. Opposed diamond anvil cells are fairly uniform in design with variations with respect to improved alignment and alignment adjustment being parameters that the operator can use in designing such cells. Accordingly, a typical cell design is set forth in the drawing wherein opposed diamond anvils 10 and 12 are seen to employ gasket 14 which confines the sample being compressed therebetween. Tilting diamond mount hemisphere 16 retains diamond anvil 12 in a recess formed therein while translating diamond mount plate 18 similarly retains diamond anvil 10 in a recess formed therein. Adjusting and alignment mechanisms, and pressure generating capability, then is applied to the cell.

Manghnani, et al., supra, state that improvements may be possible in diamond tip geometry, double beveling, and gasket design in order to achieve higher pressures. These authors further note that stronger diamond would be desirable and speculate that some advances may be made through the use of synthetic diamond. It has been found that Isotopically-pure $^{12}C$ has a smaller lattice parameter than diamond of natural isotope composition, and that diamond composed mainly of $^{13}C$ has a smaller lattice parameter and higher elastic constant than that even of diamond composed of $^{12}C$. The hardness of a material is proportional to the bond energy per unit volume. Substitution of $^{13}C$ for $^{12}C$ does not affect the bond strength, since the chemical nature of the covalent bonds do not change. Thus, the net result is that the unit volume becomes smaller and the bond energy density increases as the $^{13}C$ content increases. The lattice constant for $^{13}C$ diamond is 0.003 A smaller than the lattice constant for $^{12}C$. Consequently, $^{13}C$ diamond will have a higher bond energy density than any other diamond and, in fact, will have the highest atomic density of any known material. Thus, is should be harder than natural diamond, making it an ideal candidate for use as an anvil in high pressure cells.

Diamond enriched in $^{13}C$ (enriched in $^{13}C$ compared to natural isotopic diamond) also will have an ever decreasing lattice parameter as the $^{13}C$ content increases. The following information is relevent to this statement:

| $^{13}C$ Content (wt %) | Lattice Parameter (A) |
|---|---|
| 0.01 | 3.56713 |
| 38 | 3.56696 |
| 68 | 3.56679 |
| 99 | 3.56669 |

Thus, as diamond becomes enriched in $^{13}C$ (i.e., advantageously greater than about 5 wt-% $^{13}C$ content and preferably greater than about 10 wt-% $^{13}C$ content), the lattice parameter decreases and the hardness increases for making improved diamond anvils.

The diamond anvils can be formed of single crystal isotopically-pure $^{12}C$ or $^{13}C$ diamond, or from polycrystalline diamond made with $^{12}C$ or $^{13}C$ diamond. Isotopically pure single crystal diamond is disclosed in commonly-assigned applications Ser. No. 07/744,815, filed Aug. 12, 1991, and 547,651, filed Jul. 2, 1990. Processes disclosed therein for the manufacture of isotopically pure, single crystal diamond involve both chemical vapor deposition (CVD) processes and high pressure/-high temperature (HP/HT) processes. Isotopically-pure polycrystalline diamond is disclosed in commonly-assigned application Ser. No. 07/727,016, filed Jul. 8, 1991. The disclosures of these applications are expressly incorporated herein by reference.

An alternate process for forming the isotopically-pure diamond anvils of the present invention include converting isoptically-enriched methane (or other hydrocarbon source) to CVD diamond and using an HP/HT process with such CVD diamond feed and a single crystal seed to produce an isotopically-enriched single crystal diamond. Yet another process commences with isotopically-enriched carbon which is heated to form enriched graphite, which in turn is the feed for an HP/HT process using a single crystal seed to form an isotopically-enriched single crystal diamond.

An additional process commences with enriched carbon which is heated to form enriched graphite for use in an HP/HT process for growing an isotopically-enriched, polycrystalline diamond product. The enriched graphite also could be used to grow small diamond crystals in the HP/HT process which small crystals could be subjected to another HP/HT process to sinter the small crystals to form an isotopically-enriched polycrystalline diamond product. A further process uses enriched methane (or other hydrocarbon source) to grow CVD diamond on a single crystal shaped substrate to produce a single crystal, isotopically-enriched layer on a normal isotope substrate product. Other processes and variations on the foregoing process will be apparant to those skilled in the art and may find utility in forming the isotopically-enriched anvils of the present invention.

With respect to conventional CVD processes useful in the present invention, hydrocarbon/hydrogen gaseous mixtures are fed into a CVD reactor as an initial step. Hydrocarbon sources can include the methane series gases, e.g. methane, ethane, propane; unsaturated hydrocarbons, e.g. ethylene, acetylene, cyclohexene, and benzene; and the like. Methane, however, is preferred. Use of either carbon-12 or carbon-13 for these hydrocarbon sources is made in accordance with the precepts of the present invention. The molar ratio of hydrocarbon to hydrogen broadly ranges from about 1:10 to about 1:1,000 with about 1:100 being preferred. This gaseous mixture optionally may be diluted with an inert gas, e.g. argon. The gaseous mixture is at least partially decomposed thermally by one of several techniques known in the art. One of these techniques involves the use of a hot filament which normally is formed of tungsten, molybdenum, tantalum, or alloys thereof. U.S. Pat. No. 4,707,384 illustrates this process.

The gaseous mixture partial decomposition also can be conducted with the assistance of d.c. discharge or radio frequency electromagnetic radiation to generate a plasma, such as proposed in U.S. Pat. Nos. 4,749,587, 4,767,608, and 4,830,702; and U.S. Pat. No. 4,434,188 with respect to use of microwaves. The substrate may be bombarded with electrons during the CVD decomposition process in accordance with U.S. Pat. No. 4,740,263.

Regardless of the particular method used in generating the partially decomposed gaseous mixture, the substrate is maintained at an elevated CVD diamond-forming temperature which typically ranges from about 500° to 1,100° C. and preferably in the range of about 850° to 950° C. where diamond growth is at its highest rate in order to maximize grain size. Pressures in the range of from about 0.01 to 1,000 Torr, advantageously about 100–800 Torr, are taught in the art, with reduced pressure being preferred. Details on CVD processes additionally can be reviewed by reference to Angus, et al., "Low Pressure, Metastable Growth of Diamond and 'Diamonlike' Phases", Science, vol. 241, pages 913–921 (Aug. 19,1988); and Bachmann, et al., "Diamond Thin Films", *Chemical and Engineering News*, pages 24–39 (May 15, 1989). The disclosures of all citations herein are expressly incorporated herein by reference.

In an alternative process for producing single-crystal diamond films, high pressure techniques are employed. Reference is made to *Encyclopedia Physical Science & Technology*, vol. 6, pp 492–506 (Academic Press, Inc., 1987); Strong, The Physics Teacher, January, 1975, pp 7–13; and U.S. Pat. Nos. 4,073,380 and 4,082,185, for general descriptions of these processes. In general, these processes involve the diffusion of carbon as a source material through a liquid bath of a metallic catalyst/solvent at pressures in the order of 50–60 Kbars and temperatures in the range of about 1300°–1500° C. A negative temperature gradient, typically of about 50° C., preferably is maintained between the carbon source material and the deposition region which contains a single crystal substrete and on which crystal growth can commence. Since the highest quality diamond is preferred, conditions are chosen for a low growth rate so as to get low dislocation density or dislocation density free crystals. As in the CVD process, the carbon source material is isotopically pure $^{12}C$ or $^{13}C$. The same substrates that function under CVD conditions are candidates for use in the high pressure process, though single crystal diamond and cubic boron nitride are preferred.

Catalysts/solvents useful in this high pressure process are known in the art. They include, for example, iron; mixtures of iron with nickel, aluminum, nickel and cobalt, nickel and aluminum, and nickel and cobalt and aluminum; and mixtures of nickel and aluminum. Iron- /aluminum mixtures frequently are preferred for the production of singlecrystal diamond, with the material consisting of 95 wt-% iron and 5 wt-% aluminum being particularly preferred.

As noted above, the isotopically-pure polycrystalline diamond can be grown by CVD techniques, or can be grown by high pressure/high temperature techniques including growing the polycrystalline diamond directly, or growing the polycrystalline diamond and then sintering the diamond to form an appropriate diamond anvil. Though HP/HT techniques are well known in the art, reference to the following patents is made with respect to the provision of details on such processing conditions: U.S. Pat. Nos. 3,141,746; 3,609,818; 3,745,623; 3,831,428; and 3,850,591. The disclosures of these patents, and all other references cited herein, are expressly incorporated herein by reference.

I claim:

1. In a method for achieving high pressure wherein a sample is placed between a pair of single crystal diamond anvils compressed, the improvement which comprises forming said anvils from isotopically-enriched $^{13}C$ diamond wherein said diamond has $^{13}C$ enrichment greater than about 5 weight percent.

2. The method of claim 1 wherein said anvil is formed from isotopically-pure $^{13}C$.

3. The method of claim 1 wherein said enrichment is greater than about 10 percent.

4. The method of claim 1 wherein said diamond has a lattice parameter of greater than about 3.56696.

* * * * *